(12) United States Patent
Anissian

(10) Patent No.: US 8,979,853 B2
(45) Date of Patent: Mar. 17, 2015

(54) METHOD AND SYSTEM FOR DETERMINING RESECTION GUIDELINES FOR JOINT REPLACEMENT SURGICAL PROCEDURES

(76) Inventor: Lucas Anissian, Bloomfield Hills, MI (US)

( * ) Notice: Subject to any disclaimer, the term of this patent is extended or adjusted under 35 U.S.C. 154(b) by 1233 days.

(21) Appl. No.: 11/357,245

(22) Filed: Feb. 17, 2006

(65) Prior Publication Data

US 2007/0043375 A1  Feb. 22, 2007

Related U.S. Application Data

(60) Provisional application No. 60/653,480, filed on Feb. 17, 2005.

(51) Int. Cl.
| | | |
|---|---|---|
| *A61B 17/58* | (2006.01) | |
| *A61B 17/15* | (2006.01) | |
| *A61B 17/17* | (2006.01) | |
| *A61B 17/32* | (2006.01) | |
| *A61B 19/00* | (2006.01) | |

(52) U.S. Cl.
CPC ............ *A61B 17/15* (2013.01); *A61B 17/155* (2013.01); *A61B 17/157* (2013.01); *A61B 17/1703* (2013.01); *A61B 2017/320052* (2013.01); *A61B 2019/5437* (2013.01); *A61B 17/1764* (2013.01)
USPC .......................................... 606/88

(58) Field of Classification Search
CPC ...... A61B 17/15; A61B 17/8847; A61B 18/20
USPC ............ 606/81–102; 76/44, 31; 83/522.26, 83/522.28; 623/908, 911, 914, 919, 923; 378/204, 205
See application file for complete search history.

(56) References Cited

U.S. PATENT DOCUMENTS

| | | | | |
|---|---|---|---|---|
| 4,945,799 A | * | 8/1990 | Knetzer | 83/745 |
| 5,116,344 A | * | 5/1992 | Sundqvist | 606/130 |
| 5,141,512 A | * | 8/1992 | Farmer et al. | 606/87 |
| 5,154,717 A | * | 10/1992 | Matsen et al. | 606/53 |
| 5,520,694 A | * | 5/1996 | Dance et al. | 606/86 R |
| 5,569,260 A | * | 10/1996 | Petersen | 606/88 |
| 5,578,039 A | * | 11/1996 | Vendrely et al. | 606/88 |
| 5,598,269 A | * | 1/1997 | Kitaevich et al. | 356/399 |
| 5,606,590 A | * | 2/1997 | Petersen et al. | 378/177 |
| 5,611,353 A | * | 3/1997 | Dance et al. | 600/595 |
| 5,733,292 A | * | 3/1998 | Gustilo et al. | 606/88 |
| 5,864,956 A | * | 2/1999 | Dong | 33/227 |
| 5,887,355 A | * | 3/1999 | Wolff | 33/333 |
| 5,916,219 A | * | 6/1999 | Matsuno et al. | 606/88 |
| 5,918,523 A | * | 7/1999 | Cutter | 83/520 |
| 6,002,859 A | * | 12/1999 | DiGioia et al. | 703/11 |
| 6,027,504 A | * | 2/2000 | McGuire | 606/87 |
| 6,383,149 B1 | * | 5/2002 | DeMayo | 600/587 |
| 6,514,259 B2 | * | 2/2003 | Picard et al. | 606/88 |

(Continued)

*Primary Examiner* — Matthew Lawson
(74) *Attorney, Agent, or Firm* — R. Keith Harrison

(57) ABSTRACT

A method and system for utilizing a plurality of linear laser beams to project guidelines onto a skeletal joint for resection of the joint during surgical joint replacement. The method comprises projecting a plurality of parallel and intersecting linear laser beams along the long axis of a limb and the skeletal joint to form guidelines for the surgical resection procedure. The system comprises a plurality of devices to generate linear laser beams, integrated leveling and positioning devices, and cutting blocks and handles that are integrated with separate leveling devices. The linear laser beams establish appropriate guidelines for the joint resection.

18 Claims, 4 Drawing Sheets

(56) References Cited

U.S. PATENT DOCUMENTS

| | | | |
|---|---|---|---|
| 6,743,235 B2* | 6/2004 | Subba Rao | 606/91 |
| 6,859,661 B2* | 2/2005 | Tuke | 600/424 |
| 7,209,776 B2* | 4/2007 | Leitner | 600/407 |
| 7,392,076 B2* | 6/2008 | Moctezuma de La Barrera | 600/427 |
| 7,419,492 B2* | 9/2008 | Yoon et al. | 606/91 |
| 7,419,942 B2* | 9/2008 | Mallow et al. | 508/471 |
| 7,468,075 B2* | 12/2008 | Lang et al. | 623/16.11 |
| 2002/0052606 A1* | 5/2002 | Bonutti | 606/88 |
| 2003/0028196 A1* | 2/2003 | Bonutti | 606/87 |
| 2004/0236424 A1* | 11/2004 | Berez et al. | 623/14.12 |
| 2005/0070897 A1* | 3/2005 | Petersen | 606/53 |
| 2005/0113840 A1* | 5/2005 | Metzger et al. | 606/88 |
| 2005/0177170 A1* | 8/2005 | Fisher et al. | 606/88 |
| 2006/0025778 A1* | 2/2006 | Ferree | 606/102 |
| 2006/0184177 A1* | 8/2006 | Echeverri | 606/91 |
| 2007/0219559 A1* | 9/2007 | Heavener et al. | 606/87 |
| 2008/0255573 A1* | 10/2008 | Willett et al. | 606/96 |
| 2008/0281328 A1* | 11/2008 | Lang et al. | 606/87 |
| 2008/0281329 A1* | 11/2008 | Fitz et al. | 606/88 |
| 2008/0319491 A1* | 12/2008 | Schoenefeld | 606/86 R |

* cited by examiner

METHOD AND SYSTEM FOR DETERMINING RESECTION GUIDELINES FOR JOINT REPLACEMENT SURGICAL PROCEDURES

This application is submitted pursuant to 35 USC §119(e), and claims the benefit of the earlier-filed provisional application Ser. No. 60/653,480, filed on Feb. 17, 2005, by the same inventor.

BACKGROUND OF THE INVENTION

1. Field of the Invention

This invention relates in general to a method and an optical tool that enables physicians and surgeons to quickly and efficiently measure or establish proper alignment and angle configuration between replacement skeletal joints and skeletal tissue without utilizing mechanical implements that would otherwise be attached to the skeletal structure during a surgical replacement procedure. More specifically, the specification describes one form of the invention that relates to a method and an optical tool that generates and projects a plurality of linear laser beams, which beams are projected onto the limb or other body structure of a surgical patient to establish a reference pattern which the surgeon follows to achieve optimal alignment and ideal angle measurements for seating and insertion of a replacement skeletal joint.

2. Description of the Related Art

A. The Current Art for Surgically Creating an Accurately-Measured Angle and Seat for a Replacement Skeletal Joint.

By conservative estimates, within the United States alone, hundreds of thousands of skeletal joints are replaced by skilled orthopedic surgeons annually. Skeletal joint replacement surgical specialists each undergo several years of training and routinely perform hundreds of joint replacement procedures every year. The medical pathologies that necessitate joint replacements are many and varied, and include injury to the affected skeletal joint, degradation of supporting structures within the joint due to aging or illness, structural misalignment of the joint due to muscular, skeletal, and other imbalances, and excess stress to the affected joint resulting from repetitive use at the patient's workplace or other environment.

Notwithstanding the fact that a joint replacement surgical procedure is technically and medically complex, and further that the procedure demands years of surgical training, the process lends itself to a straightforward description and explanation. By way of example, the following description summarizes the steps taken by the surgeon to replace a knee joint. The surgeon first makes an incision and exposes the knee joint that will be replaced. Once exposed, the surgeon separates the two long bones that meet to form the knee joint, namely, the femur, which extends from the hip joint to the knee, and the tibia, which extends from the knee to the ankle. The surgeon then affixes an external alignment device to the femur by first, establishing a canal in the lower end of the femur to receive a locating device. Next, the surgeon inserts the locating device into the canal.

The alignment device is generally situated in a parallel orientation to the surgical patient's femur, and is attached external to the patient's leg. The combination of the locating device and alignment device thus creates an external structure which the surgeon uses as a guide to marry the replacement joint to the existing bone. The surgeon is working in three dimensions, and it is critical that the alignment and locating devices be affixed properly to give the surgeon the best guidelines for the next step of the procedure.

The locating device generally includes a cutting block, which includes several die-cuts, or jigs, that are used as guides for a surgical saw. The surgeon will use this saw to sever or resect the lower portion of the femur, which creates a platform of exposed bone tissue on the femur that will support the upper portion of the replacement joint. It is critical for the surgeon to make this cut at the proper angle to receive the replacement joint. The surgeon's ability to craft a proper angle on the receiving end of the femur is a critical component in the relative success of the surgical procedure. Because the angle of the cut is so critical, the surgeon will generally devote substantial amounts of time to setting the alignment device and confirming that it is properly oriented to the patient's bone structure and that the dies or jigs are lined up to guide the saw in a manner that creates the ideally-angled platform to receive the replacement joint.

The surgeon will perform a similar procedure on the patient's tibia. Specifically, the surgeon exposes the upper end of the tibia, attaches an external tibial alignment device, and attaches a cutting platform that includes analogous jigs or dies to allow the surgeon to cut an ideally-angled platform at the top of the patient's tibia to receive the replacement joint. As with the femoral alignment device, the external tibial alignment device is affixed in a generally-parallel orientation to the patient's tibia, and the angle of the cut is generally measured as an angle to the tibia As with the setting of the alignment device for the femur, the surgeon will also devote a substantial amount of time during the surgical procedure to affix the tibial alignment devices properly to create an ideal lower platform to receive the replacement joint. In any surgical procedure, however, particularly where the surgical patient is anesthetized with general anesthesia, the surgeon is balancing competing interests, namely, devoting sufficient time to performing the surgical procedure and achieving proper alignment of the replacement joint, while moving expeditiously so as not to keep the patient anesthetized any longer than is absolutely necessary. Accordingly, any methods or techniques that would enhance the surgeon's accuracy to perform a joint replacement procedure while simultaneously expediting that procedure would be highly desired.

This mechanical alignment process is the predominant methodology that is currently used in surgical joint replacements. Technicians and surgeons are developing computer-guided alignment systems, including scanning cameras that take an image of the joint and surrounding skeletal tissue and accompanying software that guides a surgical saw to make the desired cut at a correct angle. These systems are still in an experimental phase, and as such are cost-prohibitive for all but the most well-financed medical facilities. Moreover, these systems require extensive equipment installations and reconfigurations of surgical facilities. While they may be common place in future designs, it is unlikely that they will find rapid or common acceptance within the near term.

B. Commercially-available Laser-line Projection Devices.

Laser-guided projection tools and guide devices have been commercially available to the construction and building trades for many years. These tools are configured to project an illuminated bright laser line on any horizontal or vertical surfaces to give the tradesman a guideline during a construction process.

In operation, the tradesman will set the laser-projection device on a surface or support stand in the region in which he or she is working. The projection device will generally have two or three leveling devices, which devices are most frequently small fluid-filled vials that also contain a single air bubble. These hydraulic vials will be marked with a plurality of hatched lines. Each of the vials is situated along one axis of a three-dimensional configuration. The tradesman then adjusts the overall level of the device by turning set screws that variously raise or lower portions of the device. When the device itself is level, the single air bubbles in the glass vials will be situated in the exact center of the hatch-marks etched into the vials.

The projection device, which is most typically battery-operated, will then be set to project one or more bright lines across a surface. The line itself will generally be projected to be level and square in comparison to other features in the room. Alternately, if the tradesman desires, the projected line can be set at an angle that is measured against gauges on the projection device.

Although these devices generally project only a single line, it is a simple matter of optics to configure the laser projection device to project two or more bright lines. The lines can be projected to intersect each other at various angles or to run parallel along any given surface. In this manner, the tradesman can project patterns of lines across any surface that will be used as guides for the tradesman's craft.

SUMMARY OF A PREFERRED EMBODIMENT OF THE DISCLOSURE

To improve upon the limitations of current mechanical alignment systems utilized in surgical joint replacements, as described above, and to overcome other limitations that will become apparent upon reading and understanding the present specification, an embodiment of the present invention discloses a method, apparatus, and article of manufacture for a medical tool with optical guidelines for assessment of the angle, alignment and level of a surgical patient's limb or skeletal structures during joint replacement surgery or in conjunction with other medical procedures that requires accurate and precise measurements of angle and alignment. More specifically, the preferred embodiment of the present specification describes a system that allows the surgeon to project a plurality of laser lines onto a patient's limb in an orientation that guides the surgeon to prepare bone surfaces at optimal angles to receive a replacement skeletal joint. The system utilizes a tool comprising two laser-projection components that are each configured to assess angles, alignment and level. These components are commercially-available and have been previously adapted for use in the construction and other industries.

The operator first levels the tool, utilizing the hydraulic leveling guides that are common in the art. The tool projects intersecting lines in two separate axes. The positions, angles, and distances of the laser lines are controlled either remotely or directly with controls on the tools themselves. The projected laser lines direct the surgeon where to make the skeletal cuts in order to prepare the bone structure to receive replacement joint.

BRIEF DESCRIPTION OF THE DRAWINGS

Referring now to the drawings in which like reference numbers represent corresponding parts throughout.

DETAILED DESCRIPTION

In the following description of the preferred embodiment of the present invention, only one specific embodiment of the invention is described. It is to be understood that other embodiments as well as variations on the described embodiment are within the scope and bounds of the present invention, and that structural and other changes may be made to the present specification without departing from its scope.

Figure 1:
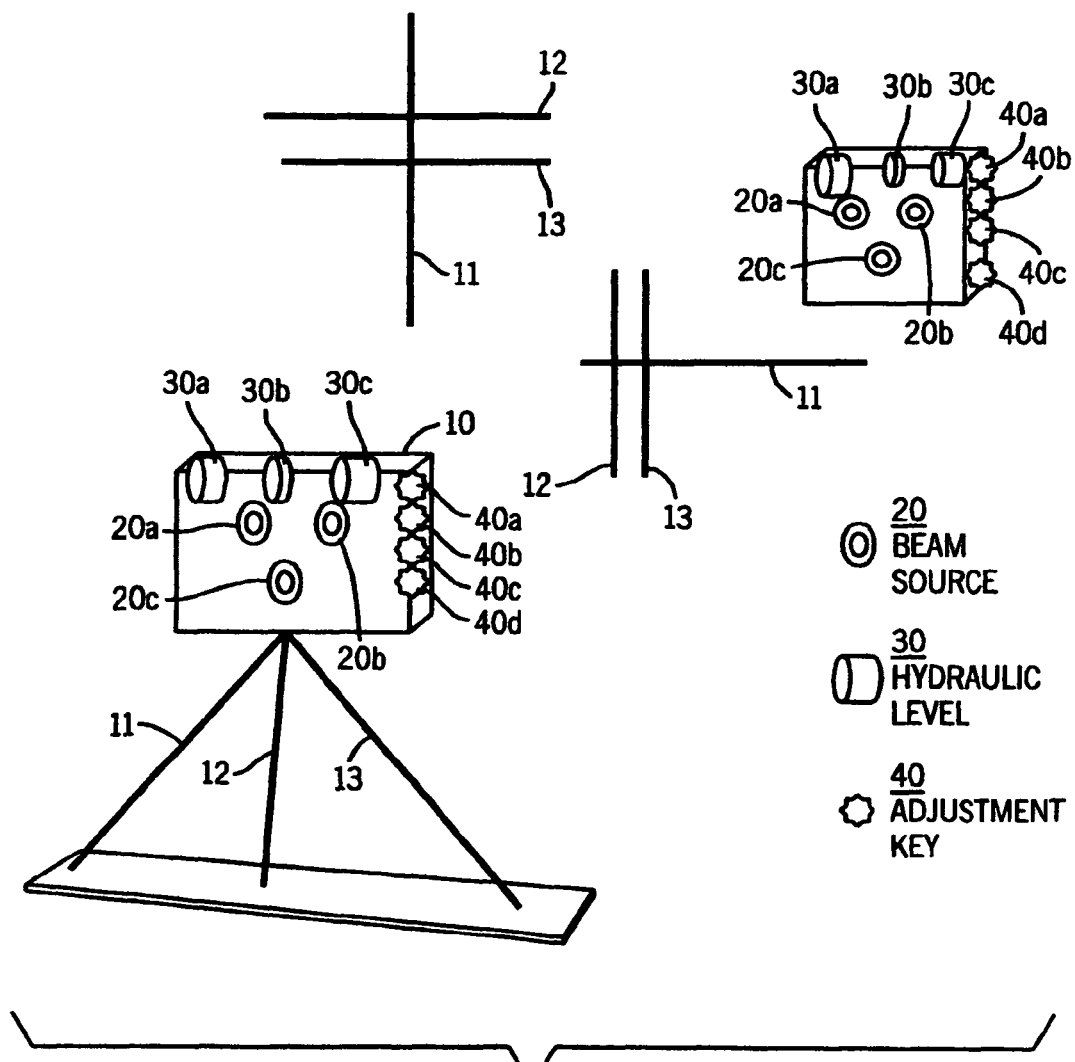
FIG. 1 is a simplified schematic diagram showing the basic components of an overhead laser light projecting system that will be configured to project linear laser beams onto a human limb.

In the preferred embodiment of the present invention, shown in FIG. 1, a laser light projecting system 10 emits three separate laser lines, 11, 12 and 13. The system 10 includes a plurality of laser beam sources, 20a, 20b, and 20c, a plurality of hydraulic leveling gauges, 30a, 30b, and 30c, and adjustment keys 40a, 40b, 40c, and 40d. During a surgical joint replacement, the surgeon will generally utilize two projecting systems 10, each of which is configured to project guiding lines across each of the skeletal bones that are being prepared to receive the replacement joint. The two systems 10 can operate dependently with each other or independently of each other. The system 10 can be directly mounted over an operating table, or it can be mounted on a portable device that is moved into position during the surgical procedure. Although the preferred embodiment of the present invention depicts the use of two separate systems 10, it is possible to configure a portable system 10 that will be used for each of the two skeletal bones that are being prepared during the procedure.

During a routine knee joint replacement procedure, the surgeon will first expose the knee joint with a routine surgical approach. The knee may be bent at an angle of ninety degrees over the operating table, or may be in full extension with no bend. The present invention works with either orientation of the joint.

Figure 2:
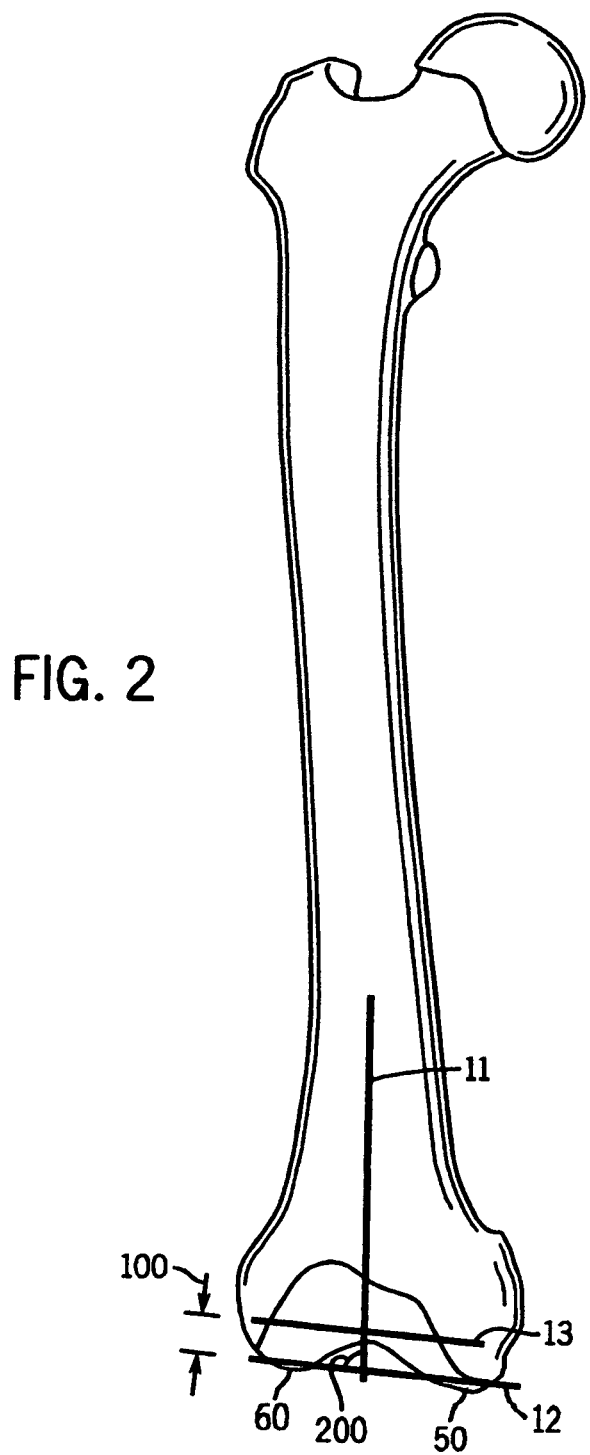
FIG. 2 is a diagram of a human femur, the lower portion of which will be prepared for receiving one section of a replacement knee joint. Intersecting laser beams are shown depicting the angle at which the lower portion of the femur will be resected.

The surgeon will then orient the system 10 to be properly balanced and leveled, and will direct the system 10 to project first laser guideline 11. The system may be affixed on an articulating arm that is secured to the ceiling of the operatory theater, or may be mounted, for example, on a tripod for more ambulatory use in the theater. As shown in FIG. 2, during preparation of the femur, first guideline 11 is generally projected in an orientation that is parallel to the long axis of the bone. This linear beam traces an anatomical axis by connecting the deepest part of the trochlear groove with the low point of the intercondylar region and the femur shaft. System 10 will then project a second guideline 12 that will generally run through a line that connects two elements, namely, the medial epicondyle 50, and lateral epicondyle 60, on the lower end of the femur, in a generally horizontal plane. The surgeon will configure system 10 to project guideline 12 at the desired angle 200 to the first guideline 11; and to project guideline 13 to a separating distance that matches the desired cutting thickness 100 and angle 200 for preparation of the lower end of the femur. The system of the present invention may be configured such that the surgeon can pre-enter the desired separating distance between guidelines 12 and 13 such that the system projects said guidelines with the pre-entered thickness. Alternately, the surgeon can manually establish the thickness with standard adjustment controls during the procedure.

The adjustment keys 40*a*, 40*b*, 40*c*, and 40*d* allow fine tuning of angle 200. Following this setup, guideline 13 will thus indicate the resection level and desirable angle for cutting the lower end of the femur. The entire process for establishing guideline 13 in the appropriate orientation and configuration substantially reduces the preparation time that would otherwise be required with mechanical alignment tools and procedures.

Once guideline 13 has been projected in the desired orientation, the surgeon will use that optical guideline to attach and secure a standard cutting block onto the distal femur with standard connecting pins. In an alternative embodiment of the system of the present invention, the surgeon utilizes a specially configured angled handle 300, which has its own leveling devices to verify proper matching of the guidelines and cutting block. The cutting block is held by the angled handle 300 while the block is being attached to the distal femur along the appropriate guideline. The surgeon then resects the distal femur in a routine fashion with an oscillating surgical saw or similar tool. To accomplish the external rotation of the cut, cutting blocks are inserted in a generally parallel fashion to guidelines 12 and 13, and the anterior, posterior and chamfer cutting is performed in the routine manner.

Figure 3:
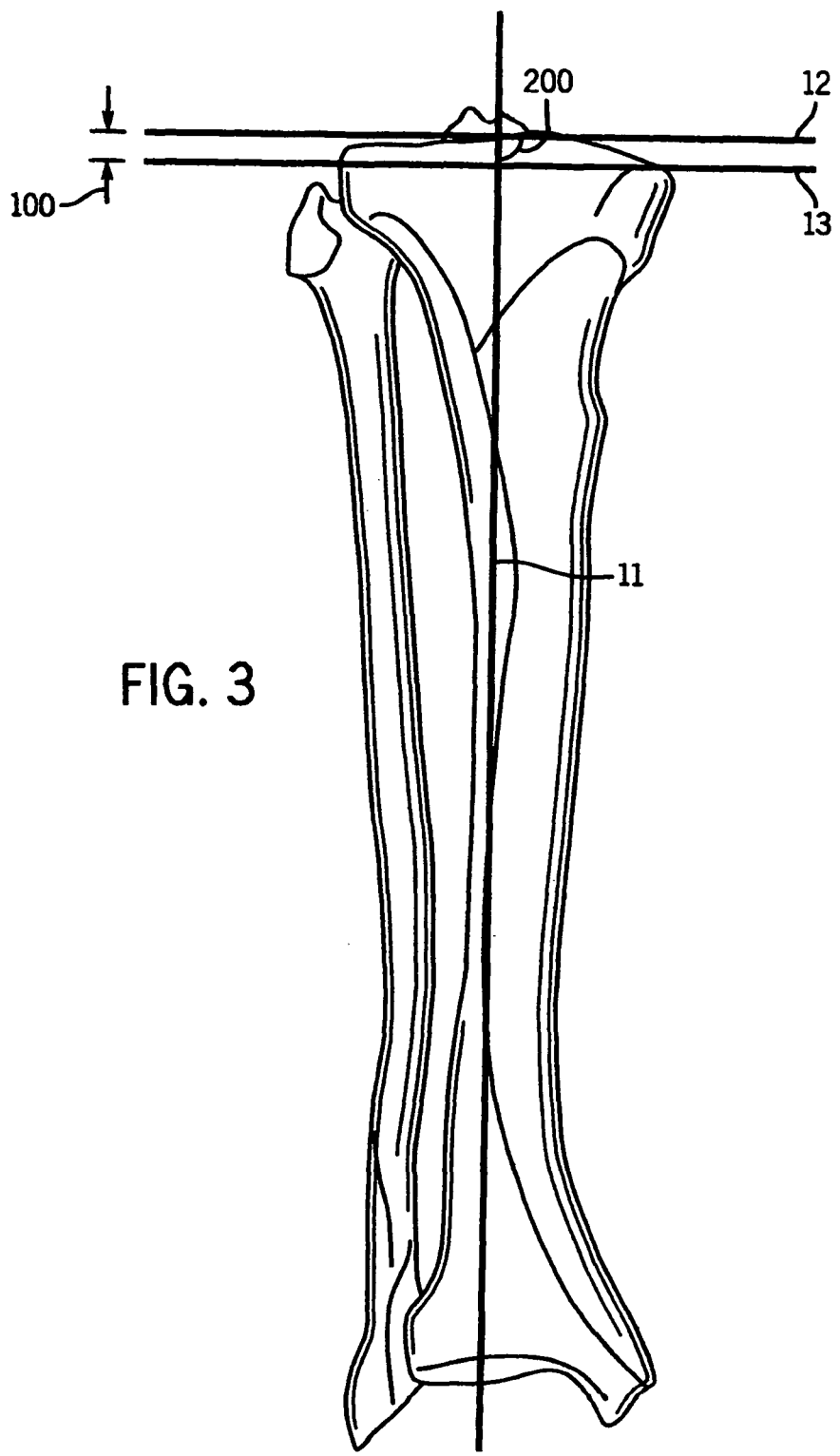
FIG. 3 is a diagram of a human tibia, the upper portion of which will be prepared for receiving a different section of the replacement knee joint. Intersecting laser beams are shown depicting the angle at which the upper portion of the tibia will be resected.
Figure 4:
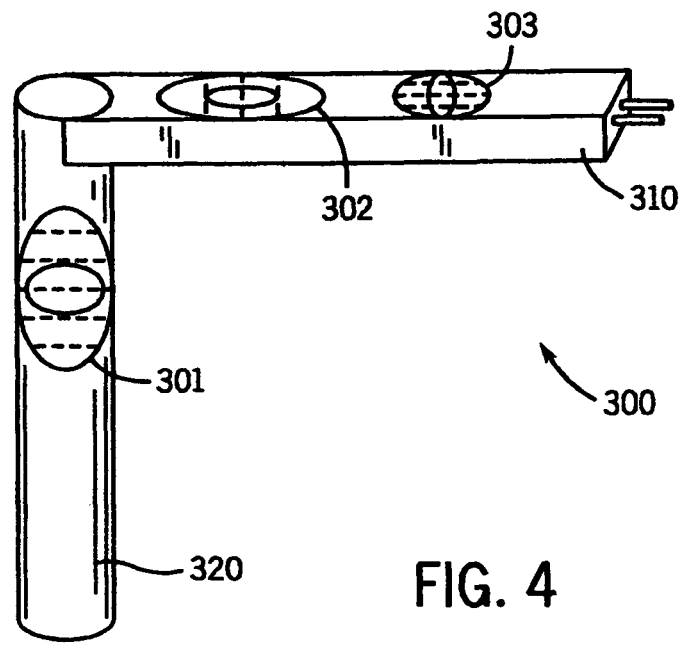
FIG. 4 depicts an angled handle that may be utilized to facilitate attachment of cutting blocks in one preferred embodiment of the present invention.
Figure 5:
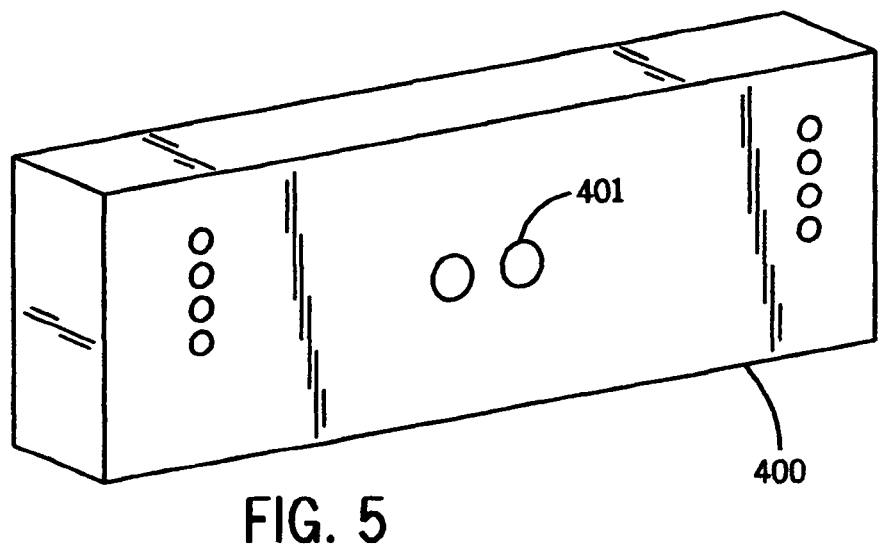
FIG. 5 is a drawing of a distal femoral cutting block, configured with a connection site for the angled handle of one preferred embodiment of the present invention.

A similar procedure is followed to prepare and resect the tibia. After exposing the top of the tibia and the knee joint with a routine surgical approach, the system 10 will be leveled and aligned over the exposed joint. As shown in FIG. 3, guideline 11 is projected along the long axis of the tibia in a generally vertical plane and in a manner that connects the center of the ankle joint to the center of the proximal tibia. The surgeon refers to common anatomical landmarks, such as the tuberosity, the anterior tibial crest, and the medial and lateral malleoluses to orient guideline 11 properly. The surgeon then configures system 10 to project guideline 12 in a generally horizontal plane along an axis that connects the medial and lateral condyles at the top of the tibia. The surgeon will configure system 10 to project guideline 12 at the desired angle 200 to the first guideline 11; and to project guideline 13 at a separating distance that matches the desired cutting thickness 100 and angle 200 for preparation of the upper end of the tibia. As with the preparation of the femur, the entire process for establishing guideline 13 in the appropriate orientation and configuration on the tibia substantially reduces the preparation time that would otherwise be required with mechanical alignment tools and procedures.

Once guideline 13 has been projected in the desired orientation, the surgeon will use that optical guideline to attach and secure a standard cutting block onto the tibia in the medial/lateral or varus/valgus directions with standard connecting pins. The handle 300 allows for accurate placement of the cutting block in the anterior and posterior directions. The surgeon then resects the tibia in a routine fashion with ban oscillating surgical saw or similar tool.

In an alternative embodiment of the present invention, the handle 300 is a useful tool to orient and hold the cutting blocks. In one preferred form, the handle comprises two arms, 310 and 320, equipped with leveling guidelines 301, 302 and 303. The arms 301 and 302 are oriented in a 90° angle to each other. A cutting block 400 can be removably attached to the handle at connection site 401 via any manner of standard removable connecting means. The leveling guidelines 301, 302 and 303 allow the surgeon to find an appropriate neutral position prior to securing the cutting block to the bone surface that will be resected. More specifically, said leveling guidelines facilitate proper positioning on a femoral or tibial anterior or posterior axis or the flexion/extension axis, as a neutral position along these axes is critical for proper determination of the angle of the cutting surface.

The foregoing specification describes an apparatus, method of use and article of manufacture that is configured for one specific use, namely, providing guidelines for bone resections during knee joint replacement surgery. The present invention may also be adapted, for example, for use in implantation of shoulder, hip, elbow, and ankle prosthetics. In practice, the invention described in this specification can further be adapted for use in any surgical procedure that requires accurate measurements of angles and cutting surfaces, and is particularly useful in procedures in which it is desirable to minimize contact between mechanical devices and multiple body parts and tissues. Because the present invention relies on projected laser guidelines rather than physical or mechanical devices, such contact with body parts and tissues is eliminated.

Further, the present invention may be adapted for other medical applications, including non-surgical applications, that require accurate and precise measurements of angle, range of motion, or deformities, including, for example, measurement of angles and deformities in spinal curvature or upper or lower extremities. By providing a system for such accurate measurement, intra-observer error is eliminated. In particular, spine deformities, such as scoliosis, are particularly amenable to accurate measurement by the system described in the present invention.

This concludes the description of the preferred embodiment of the invention. This description has been presented for purposes of illustration and description. It is not intended to be exhaustive or to limit the invention to the precise form disclosed. Many modifications and variations are possible in light of the above teaching. It is not intended that the scope of the invention will be limited by the foregoing description.

I hereby claim:

1. A method of creating guidelines for resection of a skeletal joint, wherein said joint comprises one or more bones, said bones being located in a person's limb, wherein said method includes the steps of:
   a. surgically exposing said joint;
   b. projecting a first linear laser beam from a laser light projecting system over said limb in which the joint is being resected along a long parallel axis of said limb;
   c. projecting a second linear laser beam from the laser light projecting system crossing the first linear laser beam, wherein the first linear laser beam provides a landmark for orienting a desired angle of the second linear laser beam, and the second linear laser beam runs laterally across a bone in the joint being resected and connects an end of known surgical landmarks at the end of a bone resection site;
   d. projecting a third linear laser beam from the laser light projecting system crossing the first linear laser beam and parallel to the second linear laser beam and at a distance from such second linear laser beam and laterally across the bone, wherein a gap created by the second and third linear laser beams defines a portion of the bone that will be resected and the second and third linear laser beams serve as guides for a cutting block; and e. installing the cutting block onto the joint using the first, second and third linear laser beams as guides to confirm proper placement of the cutting block onto the joint surface.

2. The method of claim 1, wherein the laser light projecting system comprises a laser beam generator which generates the first, second and third linear laser beams is fixedly mounted within an operatory theater, and wherein such system is first leveled to orient the laser beam generator along each of three axes.

3. The method of claim 2, wherein the laser beam generator which generates the first, second and third linear laser beams is portably mounted on a mounting structure, and wherein the laser light projecting system having a laser beam generator and the mounting structure are first leveled to orient the laser beam generator along each of three axes.

4. The method of claim 1 wherein the gap created by the second and third linear laser beams is pre-set prior to projecting said second and third linear laser beams onto their respective targets.

5. The method of claim 1 wherein an angled orientation of the first and second laser beams is pre-set prior to projecting said first and second linear laser beams onto their respective targets.

6. The method of claim 1, further including attaching a cutting jig onto the bone being resected and utilizing the first, second and third linear laser beams to establish proper orientation for the cutting jig.

7. The method of claim 6, further including utilizing a removable handle to facilitate attachment of the cutting jig.

8. The method of claim 1, further including repeating of the steps (a) through (d) on a second bone that is being resected.

9. A method of utilizing a plurality of projected laser beams to generate guidelines for resection of bones in a skeletal joint, said method including projecting a first linear laser beam from a laser light projecting system along one axis of a patient's limb, projecting one or more additional linear laser beams from the laser light projecting system laterally across the patient's limb and crossing the first linear laser beam, the one or more additional linear laser beams serve as guides for a cutting block and installing the cutting block onto the joint using the first. second and third linear laser beams as guides to confirm proper placement of the cutting block onto the joint surface.

10. A system for generating guidelines for resection of bones in a skeletal joint, said system comprising:
   a. a linear laser beam generating system capable of generating a plurality of linear laser beams in various orientations;
   b. at least one leveling gauge to allow for establishment of a neutral position for said linear laser beam generating system;
   c. whereby with said linear laser beam generating system a first linear laser beam is projected along a long parallel axis of the bones and second and third linear laser beams are projected in angular orientation to each other and crossing relationship to the first linear laser beam laterally across the bones within the skeletal joint of a surgical patient to generate resection guidelines, the second and third linear laser beams serve as guides for a cutting block; and
   d. a cutting block for placement on the skeletal joint, the second and third linear laser beams serve as guides to confirm proper placement of the cutting block onto the joint surface.

11. The system of claim 10 wherein such linear laser beam generating system is fixedly mounted in an operatory theater.

12. The system of claim 10 wherein such linear laser beam generating system is portably mounted on a mounting structure.

13. The system of claim 10 wherein such linear laser beam generating system generates two of the linear laser beams in a generally parallel fashion such that a gap between said linear laser beams defines a portion of a skeletal surface that will be resected.

14. The system of claim 10 wherein such linear laser beam generating system generates two of the plurality of linear laser beams in crossing relation to each other.

15. The system of claim 14 wherein an angle of the two of the plurality of linear laser beams can be measured and established to any angular measurement between 0° and 360°.

16. The system of claim 10, further including a cutting jig attachable onto a bone that is being resected, wherein an orientation of such cutting jig is established by referring to the first, second and third linear laser beams generated by such linear laser beam generating system.

17. The system of claim 16, further including a handle that is removably attached to the cutting jig, and further including a plurality of integrated leveling guidelines to set a neutral orientation of said handle and cutting jig.

18. The system of claim 10, wherein the linear laser beam generating system comprises two or more linear laser beam generating systems, each of which may be independently leveled via at least one leveling gauge, with each linear laser beam generating system being capable of projecting a plurality of linear laser beams onto bones in each side of a skeletal joint that is being resected.

* * * * *